(12) United States Patent
Tsai et al.

(10) Patent No.: US 7,714,145 B2
(45) Date of Patent: May 11, 2010

(54) 2-2'-DISUBSTITUTED 9,9'-SPIROBIFLUORENE-BASE TRIARYLDIAMINES AND THEIR APPLICATION

(75) Inventors: Ming-Han Tsai, Taipei (TW); Hao-Wu Lin, Taipei (TW); Hai-Ching Su, Taipei (TW); Chung-Chih Wu, Taipei (TW); Fu-Chuan Fang, Kaohsiung County (TW); Yuan-Li Liao, Taipei (TW); Ken-Tsung Wong, 4F., No. 180, Zhongzheng Rd., Luzhou City, Taipei County 247 (TW); Chih-I Wu, Taipei (TW); Chi-Yen Lin, Taipei (TW); Wen-Yi Hung, Sanchong (TW); Tei-Hung Hou, Taipei (TW); Wei-Jiun Chen, Tucheng (TW)

(73) Assignee: Ken-Tsung Wong, Taipei County (TW)

( * ) Notice: Subject to any disclaimer, the term of this patent is extended or adjusted under 35 U.S.C. 154(b) by 472 days.

(21) Appl. No.: 11/749,131

(22) Filed: May 15, 2007

(65) Prior Publication Data

US 2007/0262703 A1   Nov. 15, 2007

Related U.S. Application Data

(60) Provisional application No. 60/800,020, filed on May 15, 2006.

(51) Int. Cl.
*C07D 209/82* (2006.01)
*H01J 1/62* (2006.01)

(52) U.S. Cl. .............. 548/440; 548/427; 313/506; 428/690; 428/917

(58) Field of Classification Search ........... 548/427, 548/440; 313/506; 428/690, 917
See application file for complete search history.

(56) References Cited

U.S. PATENT DOCUMENTS

| | | | | |
|---|---|---|---|---|
| 7,183,010 B2 * | 2/2007 | Jarikov | .......... | 428/690 |
| 7,326,474 B2 * | 2/2008 | Kim | .......... | 428/690 |
| 7,342,355 B2 * | 3/2008 | Seo et al. | .......... | 313/504 |
| 7,399,991 B2 * | 7/2008 | Seo et al. | .......... | 257/79 |
| 7,514,863 B2 * | 4/2009 | Lee et al. | .......... | 313/504 |

* cited by examiner

*Primary Examiner*—Golam M Shameem
(74) *Attorney, Agent, or Firm*—WPAT, PC; Justin King

(57) ABSTRACT

The present invention discloses synthesis of 2,2'-disubstituted 9,9'-spirobifluorene-based triaryldiamine. First, 2,2'-diamino-9,9'-spirobifluorene, a Pd-catalyst as auxiliary and aryl halide BX are provided, wherein X is selected from the group consisting of: Cl, Br and I, B comprises one of the following group: aryl moiety, hetero cycle, multiple fused ring, multiple fused ring with hetero atom(s). Next, a substitution reaction is performed to react the 2,2'-diamino-9,9'-spirobifluorene with the aryl halide BX to produce the 2,2'-disubstituted 9,9'-spirobifluorene-based triaryldiamines. In addition, the present invention discloses organic light emitting devices comprising hole transporting material comprising 2,2'-bis(N,N-disubstituted amino)-9,9'-spirobifluorenes.

8 Claims, 5 Drawing Sheets

2-2'-DISUBSTITUTED 9,9'-SPIROBIFLUORENE-BASE TRIARYLDIAMINES AND THEIR APPLICATION

BACKGROUND OF THE INVENTION

1. Field of the Invention

The present invention is generally related to spirobifluorene derivatives, and more particularly to synthesis of 2,2'-disubstituted 9,9'-spirobifluorene-based triaryldiamine.

2. Description of the Prior Art

In general, 2,2'-disubstituted 9,9'-spirobifluorene-based triaryldiamine are synthesized from 2,2'-dihalo-9,9'-spirobifluorene. For example, 2,2'-dibromo-9,9'-spirofluorene can be prepared by direct bromination of 9,9'-spirobifluorene in the presence of a catalytic amount of ferric chloride. However, there are much difficulty in the preparation and isolation of pure 2,2'-dibromo-9,9'-spirobifluorene. Alternatively, 2,2'-dibromo-9,9'-spirofluorene can be prepared by the replacement of amino group of 2,2'-diamino-9,9'-spirobifluorene by cupric bromide following conventional Sandmeyer procedure. In addition to biphenyl-, azobenzene-, and phenol-type side products, Sandmeyer reactions are often plagued with position isomers of halide substituent. In this case, 2,2'-dibromo-9,9'-spirobifluorene was obtained together with 2,3'-dibromo-9,9'-spirobifluorene and 2,2',3'-tribromo-9,9'-spirobifluorene as well, and the separation of these isomers remains difficult and greatly hampers materials applications. Therefore, new method of forming 2,2'-disubstituted amine-9,9'-spirobifluorenes is still needed corresponding to obtain more pure compound, improve the yield and reduce manufacturing cost.

SUMMARY OF THE INVENTION

According to the above, the present invention provides a new synthesis method of 2,2'-disubstituted 9,9'-spirobifluorene-based triaryldiamines to fulfill the requirements of this industry.

One object of the present invention is to employ a novel synthesis strategy instead of using 2,2'-dihalo-9,9'-spirobifluorene. By adding Pd-catalyst as auxiliary, 2,2'-diamino-9,9'-spirobifluorene reacts with aryl halide to obtain the desired products. Thus, such process is in a simple manner and easy to practice.

Another object of the present invention is to employ 2,2'-disubstituted 9,9'-spirobifluorene-based triaryldiamine as an effective hole transporting material for electrophosphorescence. In a preferred example, blue phosphorescent OLED comprising 2,2'-bis(N,N-disubstituted amino)-9,9'-spirobifluorenes as hole transporting material having high efficiencies up to 16%, 30.6 cd/A and 26.7 lm/W are demonstrated. According to the above, the present invention does have the economic advantages for industrial applications.

According to above-mentioned objectives, the present invention discloses a method for forming 2,2'-disubstituted 9,9'-spirobifluorene-based triaryldiamines. First, 2,2'-diamino-9,9'-spirobifluorene, a Pd-catalyst as auxiliary and aryl halide BX are provided, wherein X is selected from the group consisting of: Cl, Br and I, B comprises one of the following group: aryl moiety, hetero cycle, multiple fused ring, multiple fused ring with hetero atom(s). Next, a substitution reaction is performed to react the 2,2'-diamino-9,9'-spirobifluorene with the aryl halide BX to produce the 2,2'-bis(N,N-disubstituted amino)-9,9'-spirobifluorenes. In addition, the present invention discloses organic light emitting devices comprising hole transporting material comprising 2,2'-bis(N,N-disubstituted amino)-9,9'-spirobifluorenes.

DESCRIPTION OF THE PREFERRED EMBODIMENTS

Figure 1:
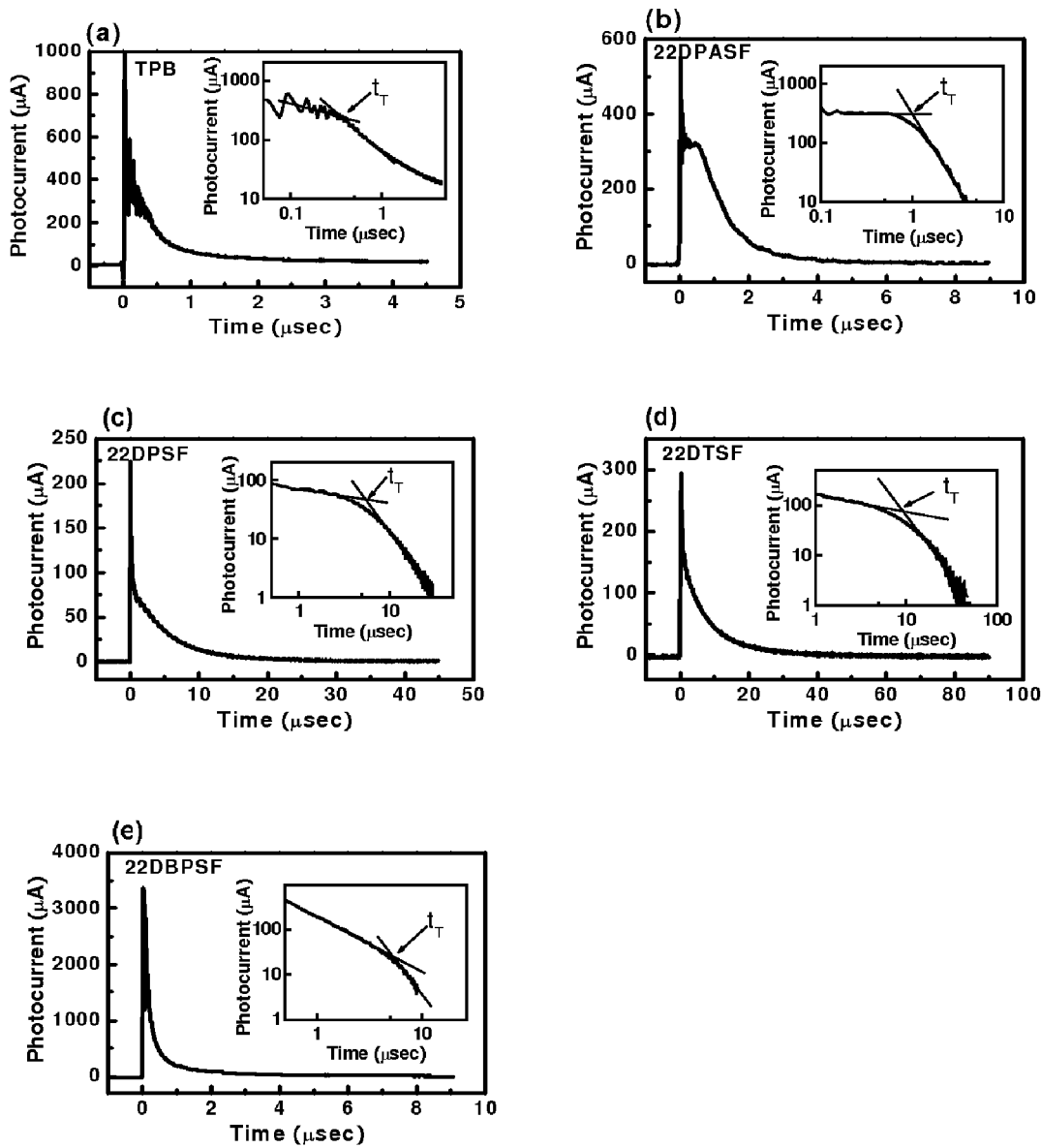
FIG. 1(a)-(e) show typical room-temperature TOF transients of holes for the 2,2'-disubstituted 9,9'-spirobifluorene-based triarylamine derivatives under an applied field, wherein (a) TPB at $E=3.3\times10^5$ V/cm, (b) 22DPASF at $E=2.5\times10^5$ V/cm, (c) 22DPSF at $E=2.5\times10^5$ V/cm, (d) 22DTSF at $E=3.3\times10^5$ V/cm, (e) 22DBPSF at $E=6\times10^5$ V/cm, and insets of (a-e) respectively are double logarithmic plots of (a-e)

What is probed into the invention is 2,2'-disubstituted 9,9'-spirobifluorene-based triaryldiamine and their application. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

According to Scheme 1, the first embodiment of the present invention discloses a method for forming 2,2'-disubstituted 9,9'-spirobifluorene-based triaryldiamine. First, 2,2'-diamino-9,9'-spirobifluorene, a Pd-catalyst as auxiliary and aryl halide BX are provided, wherein X is selected from the group consisting of: Cl, Br and I, B comprises one of the following group: aryl moiety, hetero cycle, multiple fused ring, multiple fused ring with hetero atom(s). Next, a substitution reaction is performed to react the 2,2'-diamino-9,9'-spirobifluorene with the aryl halide BX to produce the 2,2'-disubstituted 9,9'-spirobifluorene-based triaryldiamines.

Scheme 1

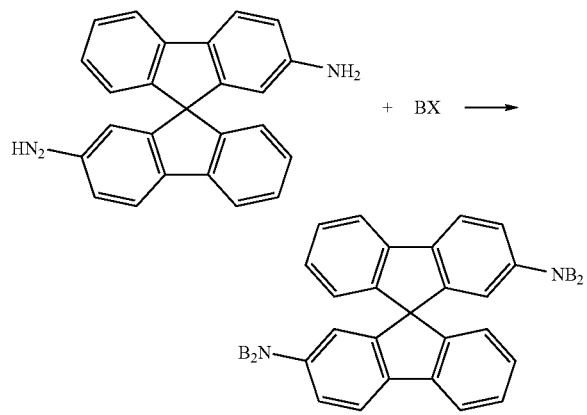

Example 1

Synthesis of 22DPSF [2,2'-Bis(diphenylamino)-9,9'-spirobifluorene]

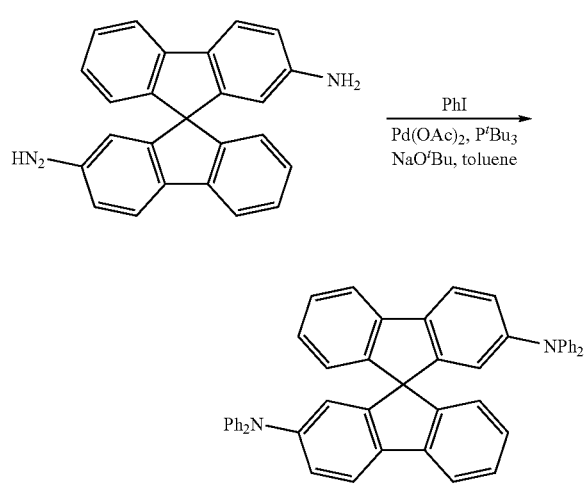

2,2'-diamino-9,9'-spirobifluorene (3.46 g, 10 mmol), iodobenzene (6.8 mL, 60 mmol), Pd(OAc)$_2$ (0.112 g, 0.5 mmol), sodium-tert-butoxide (14.4 g, 150 mmol) and tri-tert-butylphosphine (20 mL, 0.05 M in toluene, 1.0 mmol) were mixed in a flask containing with toluene (100 mL). The mixture was refluxed overnight. The solution was quenched with water and extracted twice with chloroform. The combined organic extracts were dried over MgSO$_4$ and concentrated by rotary evaporation. Column chromatography on silica gel (hexane/chloroform=4/1) afforded products [2,2'-Bis(diphenylamino)-9,9'-spirobifluorene, hereinafter named as 22DPSF] as a white solid (4.5 g, 70%).

22DPSF: m.p. 136~138° C.; IR (neat) □3071, 3045, 1593, 1493, 1440, 1295 cm$^{-1}$; $^1$H NMR (CDCl$_3$, 400 MHz) δ 7.66 (d, J=7.5 Hz, 2H), 7.61 (d, J=8.1 Hz, 2H), 7.29 (t, J=7.5 Hz, 2H), 7.18~7.14 (m, 4H), 7.06 (t, J=7.5 Hz, 2H), 7.00~6.92 (m, 7H), 6.74 (d, J=7.5 Hz, 2H), 6.65 (s, 2H); NMR (CDCl$_3$, 100 MHz) δ 149.9, 148.7, 147.6, 147.3, 141.2, 136.8, 129.0, 127.5, 126.9, 124.4, 123.7, 123.6, 122.4, 120.7, 119.9, 119.4, 65.7; MS (m/z, FAB$^+$) 650 (30), 577 (10), 549 (10), 460 (10), 369 (20), 307 (100); Anal. Calcd. C, 90.43; H, 5.27; N, 4.30. found C, 90.45; H, 5.37; N, 4.37.

Example 2

Synthesis of 22DTSF [2,2'-bis(ditolylamino)-9,9'-spirobifluorene]

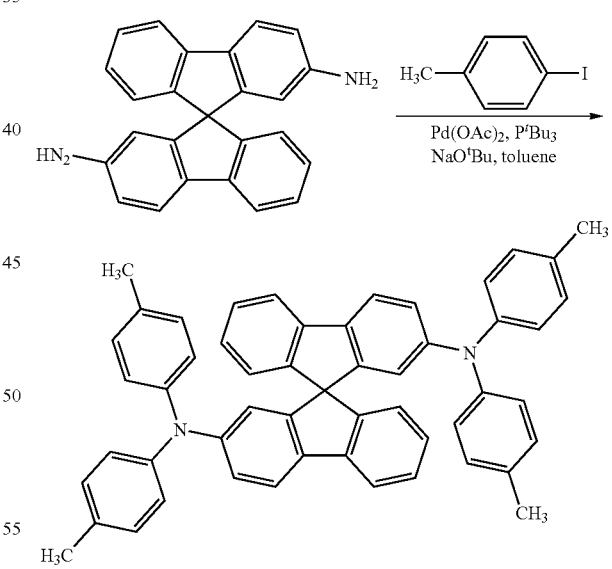

22DTSF: 2,2'□-Diamino-9,9'-spirobifluorene (3.46 g, 10.0 mmol), 4-iodotoluene (13.1 g, 60.0 mmol), Pd(OAc)$_2$ (0.112 g, 0.5 mmol), sodium-tert-butoxide (14.4 g, 150.0 mmol) and tri-tert-butylphosphine (1.0 mmol) were mixed in a flask containing with toluene (50.0 mL). The mixture was refluxed overnight. The solution was extracted twice with toluene. The combined organic extracts were dried (MgSO$_4$) and concentrated by rotary evaporation. Column chromatography on silica gel (hexane/chloroform=5/1) afforded products as white solids 22DTSF (5.9 g, 72%).

mp 259~260° C.; IR (neat) □ □3032 (w), 2925 (w), 1606 (s), 1500 (s), 1447 (s), 1314 (s), 1295 (s) cm$^{-1}$; $^1$H NMR (d$_6$-DMSO, 400 MHz) δ 7.77~7.73 (m, 4H), 7.29 (t, J=7.4 Hz, 2H), 7.06~6.99 (m, 10H), 6.83 (d, J=8.3 Hz, 2H), 6.76 (d, J=7.5 Hz, 8H), 6.58 (d, J=7.5 Hz, 2H), 6.25 (s, 2H), 2.20 (s, 12H); $^{13}$C NMR (CDCl$_3$, 100 MHz) δ 149.8, 148.9, 147.7, 145.3, 141.3, 136.1, 129.6, 127.4, 126.6, 123.7, 123.6, 123.4, 120.5, 119.2, 118.9, 65.7, 20.7; MS (m/z, FAB$^+$) 706 (30), 460 (5), 369 (5), 307 (100), 289 (60); Anal. Calcd. C, 90.05; H, 5.99; N, 3.96. found C, 90.22; H, 5.73; N, 3.74.

Example 3

Synthesis of 22DBPSF [2,2'-bis[di-(4-t-butylphenyl)amino]-9,9'-spirobifluorene]

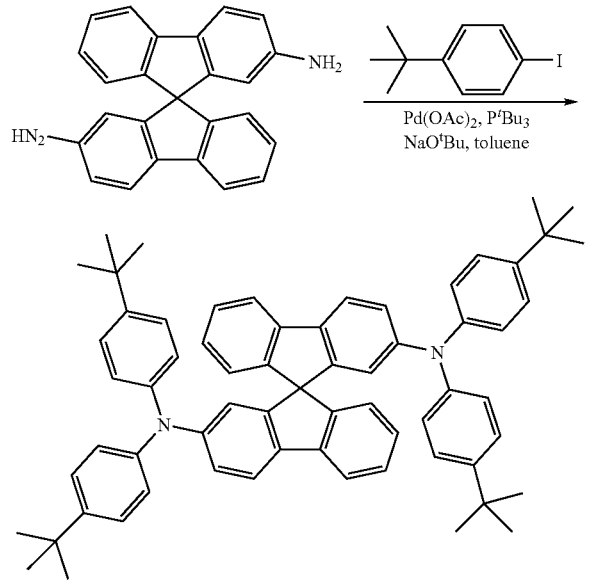

22DBPSF: 2,2'-Diamino-9,9'-spirobifluorene (3.46 g, 10.0 mmol), 4-bromo-tert-butylbenzene (10.6 mL, 60.0 mmol), Pd(OAc)$_2$ (0.112 g, 0.5 mmol), sodium-tert-butoxide (14.4 g, 150.0 mmol) and tri-tert-butylphosphine (1.0 mmol) were mixed in a flask containing with toluene (50.0 mL). The mixture was refluxed 48 hours. The solution was extracted twice with chloroform. The combined organic extracts were dried (MgSO$_4$) and concentrated by rotary evaporation. Column chromatography on silica gel (hexane/chloroform=6/1) afforded products as white solids 22DBPSF (5.3 g, 60%).

mp 286~287° C.; IR (neat) □3032 (w), 2925 (w), 1606 (s), 1500 (s), 1447 (s), 1314 (s), 1295 (s) cm$^{-1}$; $^1$H NMR (CDCl$_3$, 400 MHz) δ 7.64 (d, J=7.6 Hz, 2H), 7.58 (d, J=8.2 Hz, 2H), 7.28 (t, J=7.5 Hz, 2H), 7.16 (d, J=8.7 Hz, 8H), 7.05 (t, J=7.5 Hz, 2H), 6.96 (d, J=8.2 Hz, 2H), 6.90 (d, J=8.7 Hz, 8H), 6.74 (d, J=7.6 Hz, 2H), 6.66 (s, 2H), 1.28 (s, 18H); $^{13}$C NMR (CDCl$_3$, 100 MHz) δ 149.9, 148.8, 147.6, 145.0, 141.4, 136.3, 127.4, 126.7, 125.7, 123.9, 123.7, 122.9, 120.4, 119.6, 119.2, 65.7, 34.1, 31.4; MS (m/z, FAB$^+$) 875 (95), 859 (10), 819 (10), 580 (10), 404 (10), 250 (20); Anal. Calcd. C, 89.20; H, 7.60; N, 3.20. found C, 89.31; H, 7.68; N, 3.04.

According to Scheme 2, the second embodiment of the present invention discloses a method for forming 2,2'-disubstituted 9,9'-spirobifluorene-based triaryldiamine. First, 2,2'-di-halo-9,9'-spirobifluorene, a Pd-catalyst as auxiliary and (disubstituted amino) boronic acid are provided, wherein X is selected from the group consisting of: Cl, Br and I, Y comprises one of the following group: aryl moiety, hetero cycle, multiple fused ring, multiple fused ring with hetero atom(s), R comprises one of the following group: aryl moiety, hetero cycle, multiple fused ring, multiple fused ring with hetero atom(s). Next, a substitution reaction is performed to react the 2,2'-di-halo-9,9'-spirobifluorene with the (disubstituted amino) boronic acid to produce the 2,2'-disubstituted 9,9'-spirobifluorene-based triaryldiamines.

Scheme 2

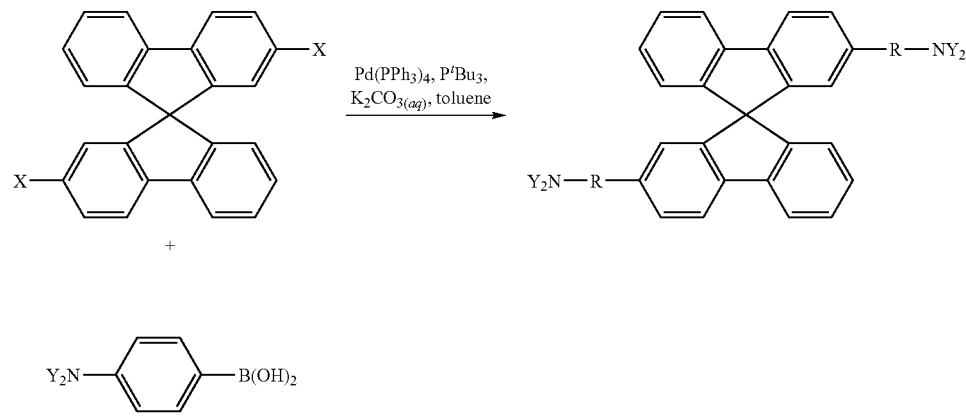

Example 4

Synthesis of 22DPASF [2,2'-bis[(diphenylaniline)-4-yl]-9,9'-spirobifluorene]

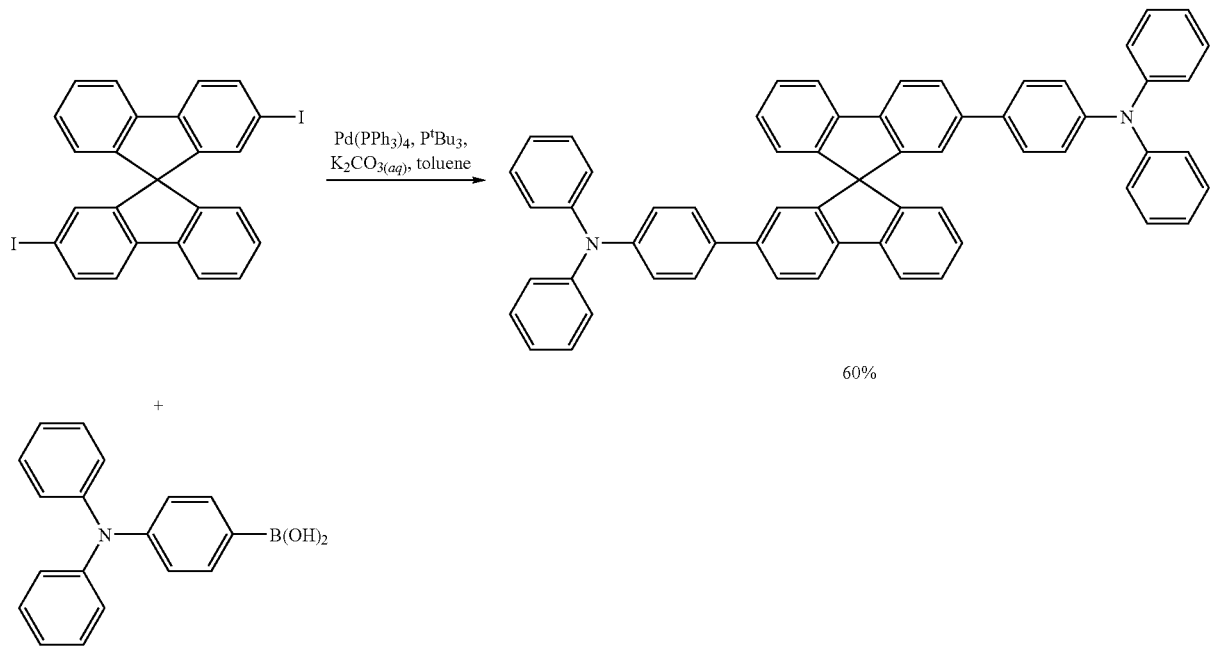

60%

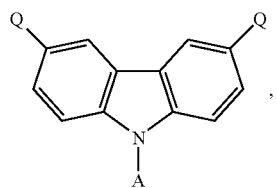

22DPASF: 2,2'-Diiodo-9,9'-spirobifluorene (2.84 g, 5.0 mmol), 4-(diphenylamino)phenylboronic acid (4.34 g, 15.0 mmol), Pd(PPh$_3$)$_4$ (0.289 g, 0.25 mmol), 2M K$_2$CO$_{3(aq)}$ (25 ml) and tri-tert-butylphosphine (0.5 mmol) were mixed in a flask containing with toluene (50.0 mL). The mixture was refluxed 72 hours. The solution was extracted twice with chloroform. The combined organic extracts were dried (MgSO$_4$) and concentrated by rotary evaporation. Column chromatography on silica gel (hexane/chloroform=3/1) afforded products as white solids 22DPASF (2.4 g, 60%).

mp 202~204° C.; IR (neat) ☐ 3071 (w), 3045 (m), 1600 (s), 1507 (s), 1487 (s), 1460 (s) cm$^{-1}$; $^1$H NMR δ 7.88 (d, J=8.0 Hz, 2H), 7.85 (d, J=7.6 Hz, 2H), 7.59 (d, J=7.8 Hz, 2H), 7.37 (t, J=7.5 Hz, 2H), 7.30 (d, J=8.5 Hz, 4H), 7.23~6.95 (m, 28H), 6.77 (d, J=7.6 Hz, 2H); $^{13}$C NMR (CDCl$_3$, 100 MHz) δ 149.5, 149.0, 147.5, 147.0, 134.9, 129.2, 127.7, 126.3, 124.2, 124.0, 123.8, 122.8, 122.2, 120.3, 119.9, 66.1; MS (m/z, FAB$^+$) 803 (100), 726 (5), 635 (5), 554 (5), 387 (5), 256 (5); HRMS (M$^+$, FAB$^+$) Calcd. C$_{61}$H$_{42}$N$_2$ 802.3348. found 802.3350.

Hole Mobility Measurement:

The charge carrier mobilities of the spirobifluorene-based triarylamines and the non-spiro model compound (tetraphenylbenzidine; TPB) with different substitutions were measured by time-of-flight (TOF) technique. FIG. 1(a)-(e) show typical room-temperature TOF transients of holes for the 2,2'-disubstituted 9,9'-spirobifluorene-based triarylamine derivatives under an applied field. We observed the photocurrent without any distinct constant current plateau, instead, the current decays significantly, resulting in dispersive charge transport, which means that the charge carriers were trapped and cannot attain their dynamic equilibrium while migrating cross the sample. The transit times (t$_T$) were obtained from the intersection point of two asymptotes in the double logarithmic representations [insets of FIG. 1(a)-(e)]. The mobilities of the charges were calculated using the relation $\mu=d^2/Vt_T$ where d is the organic film thickness, V is the applied voltage and t$_T$ is the transit time.

Figure 2:
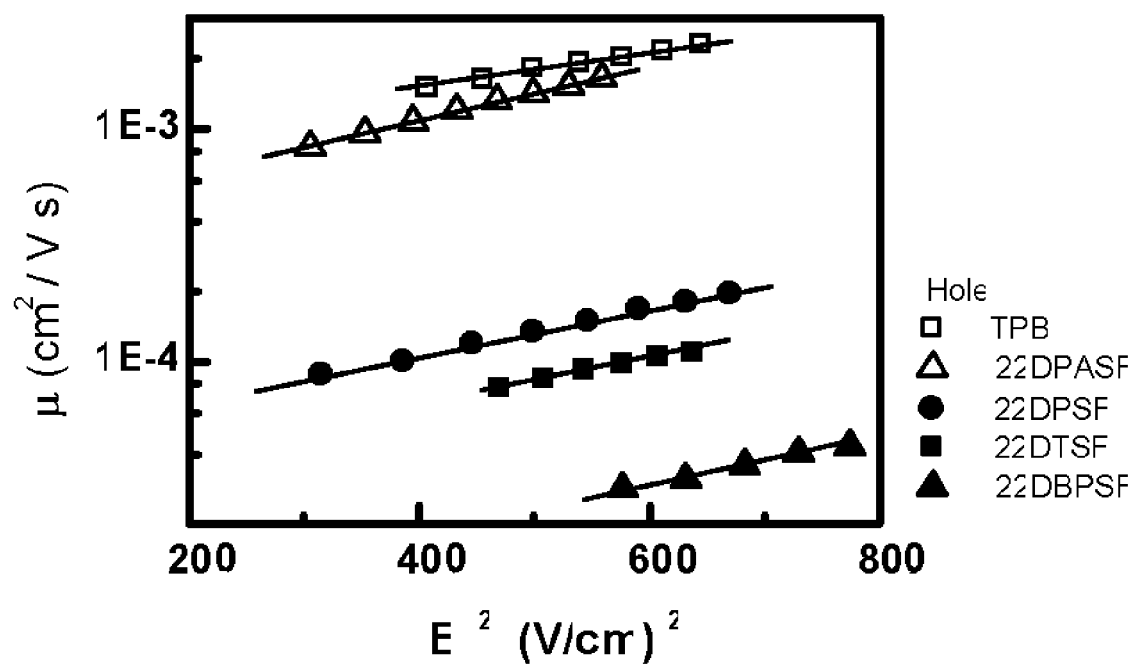
FIG. 2 summarizes the hole mobilities of the 2,2'-disubstituted 9,9'-spirobifluorene-based triarylamine derivatives and model compound TPB at room temperature against the square root of the applied electric field (the solid line is a fit by Pool-Frenkel form□)

FIG. 2 summarizes the hole mobilities of the 2,2'-disubstituted 9,9'-spirobifluorene-based triarylamine derivatives and model compound TPB at room temperature against the square root of the applied electric field, the linear correlation follows the universal Poole-Frenkel relationship: ☐μ∝☐ exp ☐βE$^{1/2}$, where β is the Poole-Frenkel factor and E is the electric field. The hole mobilities are in the range of 2×10$^{-5}$~2×10$^{-3}$ cm$^2$V$^{-1}$s$^{-1}$ for fields varying from 10$^5$ to 6.4×10$^{-5}$ V/cm. In contrast to the cases of holes, the TOF transient for electrons of the present studied samples showed strong dispersive photocurrent.

The third embodiment of the present invention discloses an organic light emitting device comprising a multilayer structure for producing electroluminescence, wherein the multilayer structure comprises: a substrate, an anode layer, a first hole transporting layer comprising 2,2'-disubstituted 9,9'-spirobifluorene-based triaryldiamine (which is described in the first and the second embodiments), a second hole transporting layer, an emitting layer comprising a host material and a guest material, wherein the host material comprises carbazole-based compound, an electron transporting layer, and a cathode layer. Moreover, the general formula of the carbazole-based compound is as following:

wherein Q of the carbazole-based compound is a non-conjugate moiety, A comprises one of the following group: aryl moiety, hetero cycle, multiple fused ring, multiple fused ring with hetero atom(s). Additionally, the glass transition temperature of the carbazole-based compound is equal to or higher than 100° C.

In a preferred example of this embodiment, the carbazole-based compound has a general formula as following:

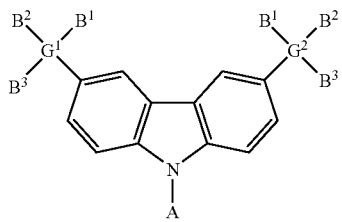

wherein $G^1$ and $G^2$ are identical or different, $G^1$ and $G^2$ are independently selected from C, Si. $B^1$, $B^2$ and $B^3$ are identical or different, and $B^1$, $B^2$ and $B^3$ are independently selected from the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or carbamates.

In another preferred example of this embodiment, the carbazole-based compound has a general formula as following:

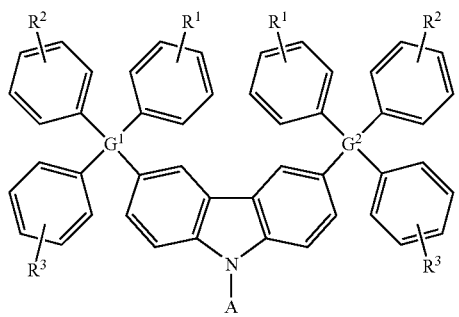

wherein $G^1$ and $G^2$ are identical or different, $G^1$ and $G^2$ are independently selected from C, Si. $R^1$, $R^2$ and $R^3$ are identical or different, and $R^1$, $R^2$ and $R^3$ are independently selected from the group consisting of: hydrogen atom, alkoxyl group, $NR^2$ (R is alkyl or aryl), linear alkyl, branched alkyl, cyclic alkyl, aryl moiety, hetero cycle, multiple fused ring, multiple fused ring with hetero atom(s), and alkyl with at least one substituent of alkene or alkyne or carbamates. Furthermore, in another preferred example of this embodiment, the carbazole-based compound is 9-(4-tert-butylphenyl)-3,6-bis(triphenylsilyl)-9H-carbazole (hereinafter named as CzSi), and has chemical structure as following:

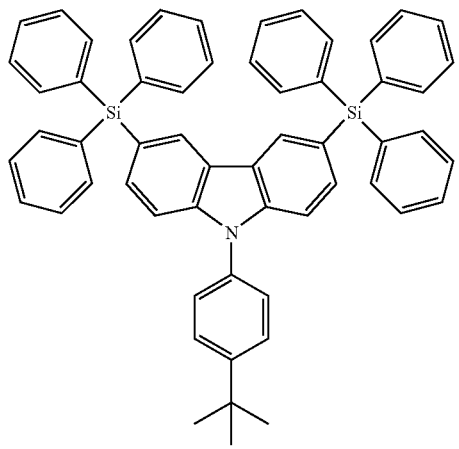

In this embodiment, the chemical structure of one preferred example of the 2,2'-disubstituted 9,9'-spirobifluorene-based triaryldiamine is as the following:

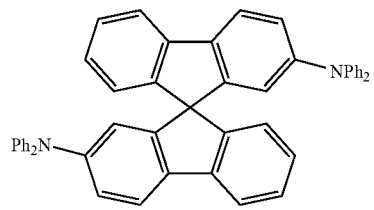

The second hole transporting layer can comprise 4,4',4"-tri (N-carbazolyl) triphenylamine (TCTA). The guest material comprises iridium(III)bis[4,6-difluorophenyl]-pyridinato-N, $C^{2'}$]picolinate (FIrpic).

Example 5

Figure 3:
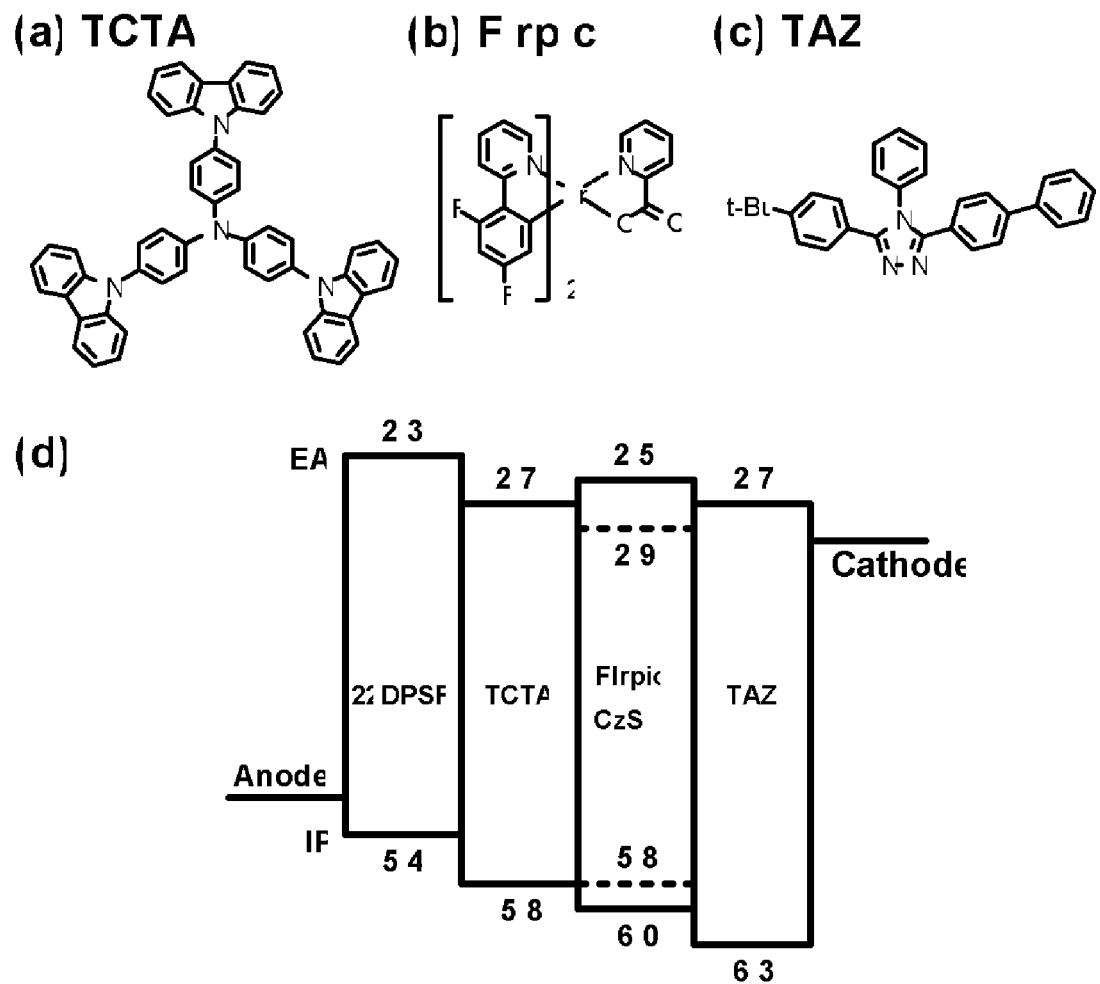
FIG. 3 shows chemical structures of (a) TCTA, (b) FIrpic and (c) TAZ. (d) Energy levels of related compounds in thin films.

The OLEDs were fabricated on glass substrates with the typical structure of multiple organic layers sandwiched between the bottom indium tin oxide (ITO) anode and the top metal cathode (Al). The PEDT:PSS layer was prepared by spin coating, and other material layers were deposited by vacuum evaporation in a vacuum chamber with a base pressure of <$10^{-6}$ torr. The deposition system permits the fabrication of the complete device structure in a single vacuum pump-down without breaking vacuum. The deposition rate of organic layers was kept at ~0.2 nm/s. The active area of the device is 2×2 mm², as defined by the shadow mask for cathode deposition. The device structure used was ITO/PEDT:PSS (~300 Å)/22DPSF (175 Å)/TCTA (25 Å)/CzSi doped with 8 wt. % FIrpic (250 Å)/TAZ (500 Å)/LiF (5 Å)/Al (1500 Å), where the conducting polymer polyethylene dioxythiophene/polystyrene sulphonate (PEDT:PSS) was used as the hole-injection layer, 22DPSF, and 4,4',4"-tri(N-carbazolyl) triphenylamine (TCTA) as the hole-transport layers, CzSi with a nearly optimized concentration (8 wt. %) of FIrpic as the emitting layer, 3-(4-biphenylyl)-4-phenyl-5-(4-tert-butylphenyl)-1,2,4-triazole (TAZ) as the electron-transport layer, and LiF as the electron-injection layer. Chemical structures of related compounds and their energy levels are shown in FIG. 3, in which ionization potentials (IP) of molecular compounds in films were determined by our own measurements with ultraviolet photoemission spectroscopy while IP of FIrpic was taken from the literature. Electron affinities (EA) of all compounds were derived by subtracting IP's with optical energy gaps.

IP's of thin films of organic compounds were measured by ultraviolet photoemission spectroscopy (UPS). The deposition and the UPS measurements of thin-film samples were performed in two interconnected ultra-high vacuum chambers. Organic thin films were deposited on gold-coated silicon substrates by thermal evaporation in the deposition chamber, and then transferred in situ to the analysis chamber. In the analysis chamber with base pressure less than 1×$10^{-10}$ Torr, UPS was carried out using the He I (21.22 eV) and He II (40.8 eV) photon lines and the double-pass cylindrical mirror analyzer to measure energy spectrum of photo-excited electrons. The overall resolution of the UPS measurement is about 0.15 eV. The energy scale of UPS spectra is referenced to the Fermi level of the system, which is measured on the gold surface before deposition of organic thin films. IP's of molecular films can be deduced from the energy difference between the HOMO level and the vacuum level (inferred from the low-energy onset of the UPS spectrum).

Figure 4:
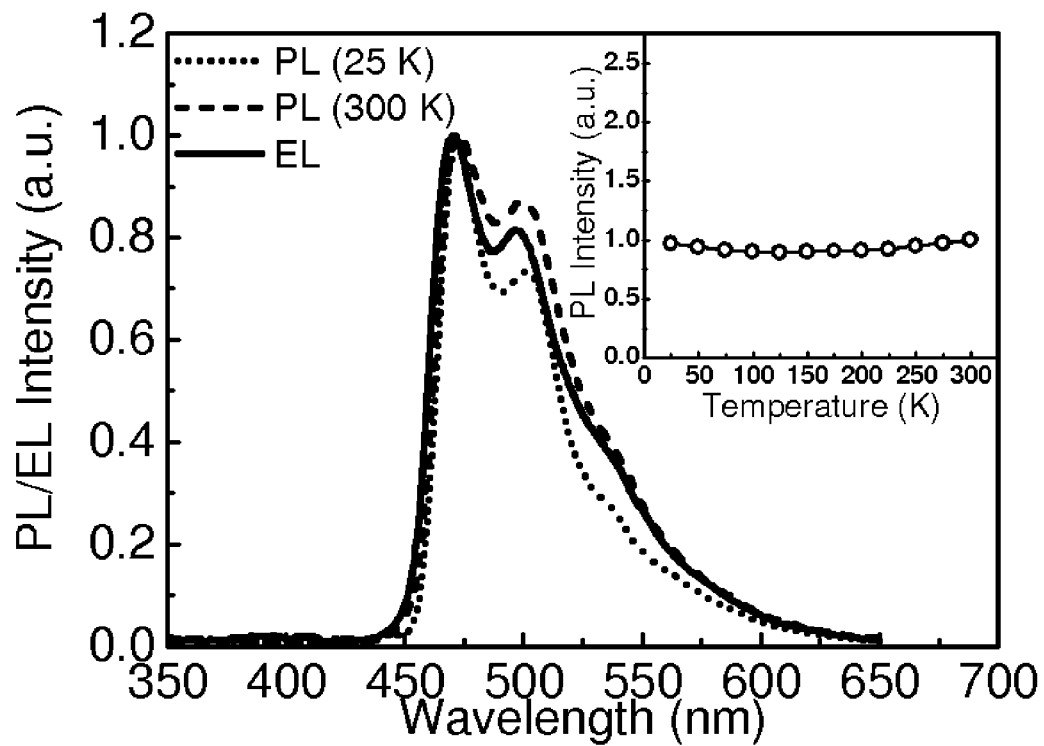
FIG. 4 shows PL spectra of a CzSi film doped with 8 wt. % of FIrpic at the room temperature and 25 K, along with the EL spectrum of the device, and the Inset is PL intensity of the FIrpic-doped CzSi film as a function of temperature.
Figure 5:
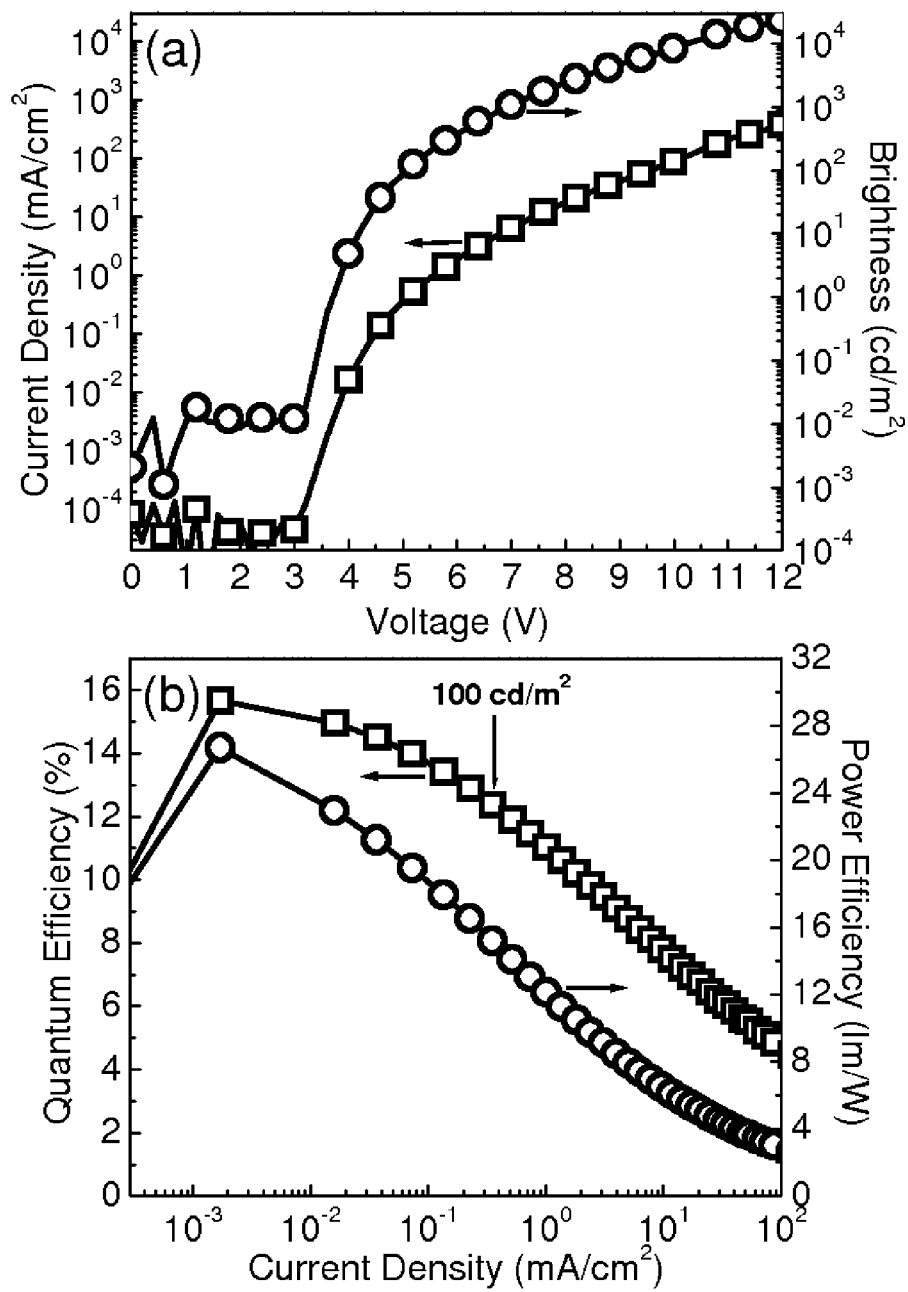
FIG. 5 shows (a) I-V-L characteristics, and (b) external EL quantum efficiency/power efficiency vs. current density of the device.

As shown in FIG. 4, EL of the device using the 22DPSF/TCTA hole-transport layers is identical to PL of FIrpic-doped CzSi, indicating the effectiveness of the present device structure in injecting both holes and electrons into the emitting layer. I-V-L characteristics, external EL quantum efficiency and power efficiency of the device are shown in FIG. 5(a) and FIG. 5(b). The current-voltage-brightness (I-V-L) characterization of the light-emitting devices was performed with a source-measurement unit (SMU) and a Si photodiode calibrated with Photo Research PR650. EL spectra of devices were collected by a calibrated CCD spectragraph. The present device exhibits a rather low turn-on voltage of ~3 V (defined as the voltage where EL becomes detectable) and a low operation voltage (100 cd/m$^2$ at 5V), as shown in FIG. 5(a). A high external EL quantum efficiency of 15.7% photon/electron (30.6 cd/A, maximum) and a maximum brightness as high as ~59000 cd/m$^2$ (at 14.5 V) were observed. High quantum efficiency along with low voltage gives maximal power efficiency of 26.7 lm/W. In addition to achieving an external quantum efficiency among the highest ever reported for blue electrophosphorescence, the power efficiency of the present device is also nearly double of the highest values previously reported for blue electrophosphorescence (~14 lm/W). These improved characteristics may, in part, be attributed to the judicious use of two hole-transport layers (22DPSF/TCTA) with a stepwise increase in IP's to match IP of CzSi, and choice of the electron-transport layer (TAZ). Using only single hole-transport layer of 22DPSF or TCTA results in lower efficiency and higher voltage. Adopting other electron-transport and hole-blocking layers widely used in phosphorescent OLEDs, such as BCP (2,9-dimethyl-4,7-diphenyl-1,10-phenanthroline) or TPBI (2,2',2"-(1,3,5-benzenetriyl)tris[1-phenyl-1H-benzimidazole]), also substantially reduces the device efficiency. Efficiency roll-off at higher currents, which is typical in phosphorescent OLEDs and may be associated with triplet-triplet annihilation, is also observed here, yet at the practical brightness of 100 cd/m$^2$ (5 V, 0.36 mA/cm$^2$), the efficiencies remain above 12%, 24 cd/A and 16 lm/W.

In the embodiments, the present invention employs a novel synthesis strategy instead of using 2,2'-dihalo-9,9'-spirobifluorene. By adding Pd-catalyst as auxiliary, 2,2'-diamino-9,9'-spirobifluorene reacts with aryl halide to obtain the desired products. Thus, such process is in a simple manner and easy to practice. On the other hand, this invention applies 2,2'-bis(N,N-disubstituted amino)-9,9'-spirobifluorenes as an effective hole transporting material for electrophosphorescence. In a preferred example, blue phosphorescent OLED comprising 2,2'-bis(N,N-disubstituted amino)-9,9'-spirobifluorenes as hole transporting material having high efficiencies up to 16%, 30.6 cd/A and 26.7 lm/W are demonstrated. According to the above, the present invention does have the economic advantages for industrial applications.

To sum up, the present invention discloses a method for forming 2,2'-bis(N,N-disubstituted amino)-9,9'-spirobifluorenes. First, 2,2'-diamino-9,9'-spirobifluorene, a Pd-catalyst as auxiliary and aryl halide BX are provided, wherein X is selected from the group consisting of: Cl, Br and I, B comprises one of the following group: aryl moiety, hetero cycle, multiple fused ring, multiple fused ring with hetero atom(s). Next, a substitution reaction is performed to react the 2,2'-diamino-9,9'-spirobifluorene with the aryl halide BX to produce the 2,2'-bis(N,N-disubstituted amino)-9,9'-spirobifluorenes. In addition, the present invention discloses organic light emitting devices comprising hole transporting material comprising 2,2'-disubstituted 9,9'-spirobifluorene-based triaryldiamines.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A light-emitting device comprising a pair of electrodes and one or more organic layers disposed between said electrodes, said one or more organic layers comprising a light-emitting layer, wherein at least one of said one or more organic layer comprises a hole transporting layer with a 2,2'-disubstituted 9,9'-spirobifluorene-based triaryldiamine with a moiety represented by the following formula:

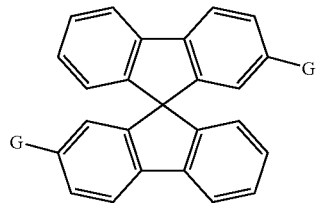

wherein G is selected from

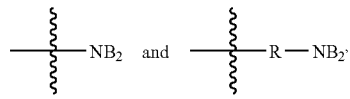

wherein B comprises one of the following group: aryl moiety, hetero cycle, multiple fused ring, multiple fused ring with hetero atom(s) and R comprises one of the following group: aryl moiety, hetero cycle, multiple fused ring, multiple fused ring with hetero atom(s).

2. The light-emitting device as claimed in claim 1, wherein B is

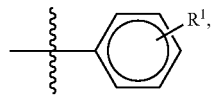

wherein R$^1$ is selected from the group consisted of hydrogen atom, alkyl moiety and aryl moiety.

3. The light-emitting device as claimed in claim 1, wherein B is

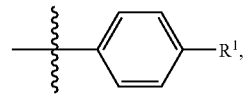

wherein R$^1$ is selected from the group consisted of hydrogen atom, methyl and tert-butyl moiety.

4. The light-emitting device as claimed in claim 1, wherein said hole transport layer further comprises 4,4',4"-tri(N-carbazolyl)triphenylamine (TCTA).

5. The light-emitting device as claimed in claim 1, wherein said light-emitting layer comprises a host material with a carbazole-based compound with a moiety represented by the following formula:

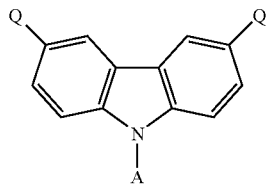

wherein Q is a non-pi-conjugated moiety, A comprises one of the following groups: aryl moiety, hetero cycle, multiple fused ring, multiple fused ring with hetero atom(s).

6. The light-emitting device as claimed in claim 5, wherein said carbazole-based compound has a general formula as following:

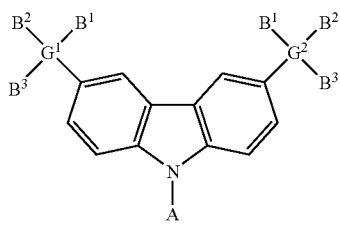

wherein $G^1$ and $G^2$ are identical or different, $G^1$ and $G^2$ are independently selected from C, Si; and $B^1$, $B^2$ and $B^3$ are either identical or different from one another, and $B^1$, $B^2$ and $B^3$ are independently selected from the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or carbamates.

7. The light-emitting device as claimed in claim 5, wherein the carbazole-based compound has a general formula as following:

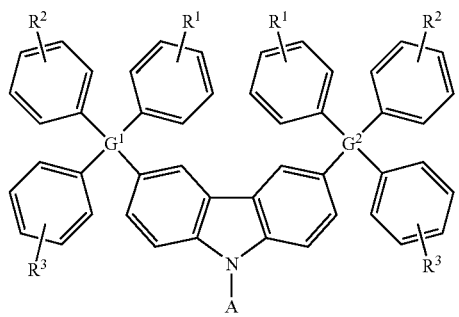

wherein $G^1$ and $G^2$ are identical or different, $G^1$ and $G^2$ are independently selected from C, Si; and $R^1$, $R^2$ and $R^3$ are either identical or different from one another, and $R^1$, $R^2$ and $R^3$ are independently selected from the group consisting of: hydrogen atom, linear alkyl, branched alkyl, cyclic alkyl, aryl moiety, hetero cycle, multiple fused ring, multiple fused ring with hetero atom(s), and alkyl with at least one substituent of alkene or alkyne or carbamates.

8. The light-emitting device as claimed in claim 5, wherein said carbazole-based compound is as following:

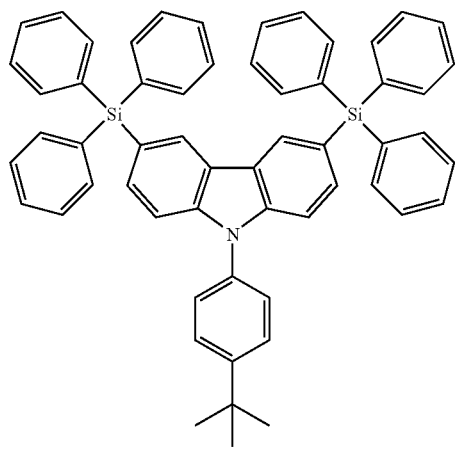

* * * * *